United States Patent [19]

Hauske

[11] Patent Number: 5,359,060
[45] Date of Patent: Oct. 25, 1994

[54] PHOSPONATED DERIVATIVES OF MACROLIDES

[75] Inventor: James R. Hauske, New York, N.Y.

[73] Assignee: Pfizer, Inc., New York, N.Y.

[21] Appl. No.: 88,011

[22] Filed: Jul. 6, 1993

[51] Int. Cl.$^5$ .................. C07D 498/16; A61K 31/395
[52] U.S. Cl. .................................................. 540/456
[58] Field of Search ......................................... 540/456

[56]  References Cited
U.S. PATENT DOCUMENTS

| | | | |
|---|---|---|---|
| 4,894,366 | 1/1990 | Okuhara et al. | 540/456 |
| 5,011,844 | 4/1991 | Fehr | 540/456 |

FOREIGN PATENT DOCUMENTS 0323042  7/1984  European Pat. Off. ............ 540/456

Primary Examiner—Robert T. Bond
Attorney, Agent, or Firm—Peter C. Richardson; Paul Ginsburg; Garth Butterfield

[57] ABSTRACT

Macrolides of formula (I) and methods of treatment of resistance to transplantation, fungal infections and autoimmune diseases such as rheumatoid arthritis and psoriasis using said macrolides of formula (I),

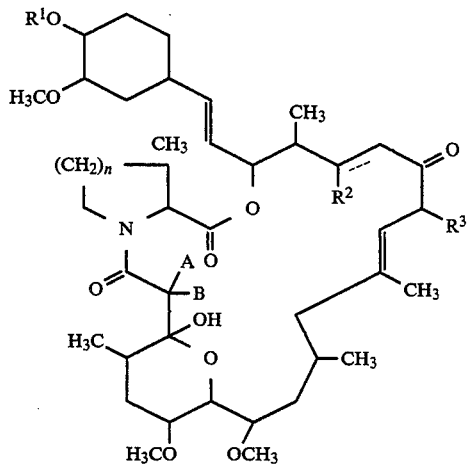

wherein n is 1 or 2; A and B taken together form =O or A and B taken separately are each H or A is OH and B is H; $R^1$ is a group of the formula

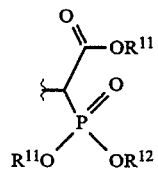

$R^2$ is OH or a desosaminyloxy group; and $R^3$ is an alkyl or allyl group.

4 Claims, No Drawings

PHOSPONATED DERIVATIVES OF MACROLIDES

BACKGROUND OF THE INVENTION

This invention relates to phosphonated derivatives of macrolides. These compounds are useful as immunosuppressive agents.

The compounds of this invention are useful in preventing or treating graft rejection following skin and organ transplant surgery and in preventing or treating autoimmune diseases such as rheumatoid arthritis and psoriasis. They are also useful in preventing or treating infectious diseases caused by fungi.

Graft or organ transplant rejection following transplant surgery is a common occurrence which arises when foreign antigens are recognized by the host's immune response system. The host's immune response system, in an effort to protect itself from the foreign tissue, then releases a cellular and humoral arsenal, resulting in complications which often end in rejection of said tissue.

The occurrence of immunoregulatory irregularities in autoimmune and chronic inflammatory diseases is well known. Treatments which target the immune response system often result in a complete shutdown of the system, leading to a lowering of the body's ability to combat infection. This can be as dangerous as the original condition which led to the shutdown. Currently, the leading medicinal agent for the prevention or treatment of graft rejection is cyclosporin A, approved by the United States Food and Drug Administration in 1983. Cyclosporin can cause kidney failure, liver damage and ulcers; which in many cases can be very severe. Safer drugs that are more selective in their ability to affect the immune response system and which have fewer side effects are constantly being pursued.

U.S. Pat. No. 4,894,366, which issued on Jan. 16, 1990, describes the macrolides FK-506 and FK-520, inter alia, as immunosuppressants which are useful in the treatment of "resistance to transplantation," autoimmune diseases and infectious diseases.

SUMMARY OF THE INVENTION

The present invention is directed to compounds of the formula

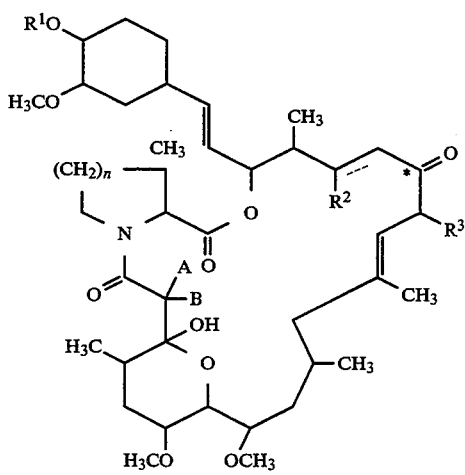

or a pharmaceutically acceptable salt thereof;

wherein n is 1 or 2;
A is H and B is H or —OH, or A and B taken together form an oxo moiety (=O);
$R^1$ is a group of the formula

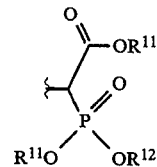

$R^2$ is H or ($C_2$–$C_5$)alkanoyloxy, wherein the dotted line represents an optional double bond in the case where $R^2$ is H;
$R^3$ is ($C_1$ to $C_3$)alkyl or allyl;
$R^{11}$ is independently selected from ($C_1$–$C_3$)alkyl; and
$R^{12}$ is ($C_1$–$C_3$)alkyl or a group of the formula

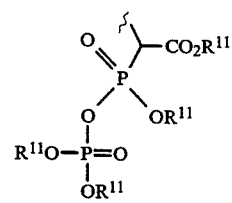

A preferred group of compounds of this invention is the group of compounds of formula I wherein $R^2$ is —OH and the dotted line represents no bond. When the dotted line represents no bond, there is a single bond between the carbon to which $R^2$ is attached and the adjacent carbon that is also adjacent to the carbon at the position marked with an asterisk (*).

A more preferred group of compounds of this invention are the compounds where A and B are taken together and form an oxo moiety (=O), n is 2 and $R^3$ is ethyl.

A still more preferred group of compounds of this invention are those compounds wherein $R^1$ is

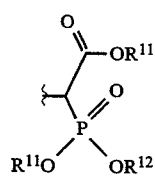

and wherein $R^{12}$ is ($C_1$–$C_3$)alkyl.

The present invention also relates to a method of treating resistance to transplantation in a mammal, preferably a human, in need of such treatment comprising administering to said mammal an immunosuppressive effective amount of a compound of formula I or a pharmaceutically acceptable salt thereof.

This invention also relates to a pharmaceutical composition comprising an immunosuppressive effective amount of a compound of formula I and a pharmaceutically acceptable carrier.

The term "transplantation," as used herein, refers to the implantation in one part of an individual of a tissue or organ taken from another part of that individual or from another individual. Typical transplantations include, but are not limited to, transplantations of bone marrow, heart, renal, tendon and pancreaticoduodenal.

The term "graft", as used herein, refers to any unattached tissue or organ which is used for transplantations. Typical grafts include, but are not limited to, skin, bone, fat and nerve grafts.

The term "treatment", as used herein, includes preventative treatment.

The present invention also relates to a method of treating an autoimmune disease (such as rheumatoid arthritis, asthma, inflammatory bowel disease, lupus erythematosus or psoriasis) in a mammal, including a human, in need of such treatment, comprising administering to said mammal an immunosuppressive effective amount of a compound of formula I or a pharmaceutically acceptable salt thereof.

The present invention also relates to a pharmaceutical composition comprising an autoimmune disease treating effective amount of a compound of formula I and a pharmaceutically acceptable carrier.

The present invention also relates to a method of treating a disease caused by fungi in a mammal, including a human, in need of such treatment comprising administering to said mammal an antifungal effective amount of a compound of formula I or a pharmaceutically acceptable salt thereof.

Additionally, this invention embraces a pharmaceutical composition comprising an antifungal effective amount of a compound of formula I and a pharmaceutically acceptable carrier.

The present invention also relates to the pharmaceutically acceptable base addition salts of compounds of the formula I. Examples of pharmaceutically acceptable base addition salts are the alkali metal salts, (e.g., sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine.

With respect to the macrolides of formula (I) of this invention, there are conformer(s) or stereoisomeric forms such as optical and geometrical isomers due to asymmetric carbon atoms(s) and double bond(s). Such isomers are also included within the scope of this invention.

DETAILED DESCRIPTION

The compounds of formula I of the present invention are readily prepared from macrolides of formulae X or XI

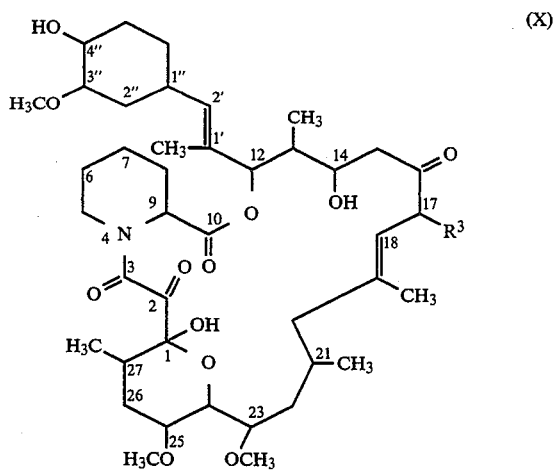

(X)

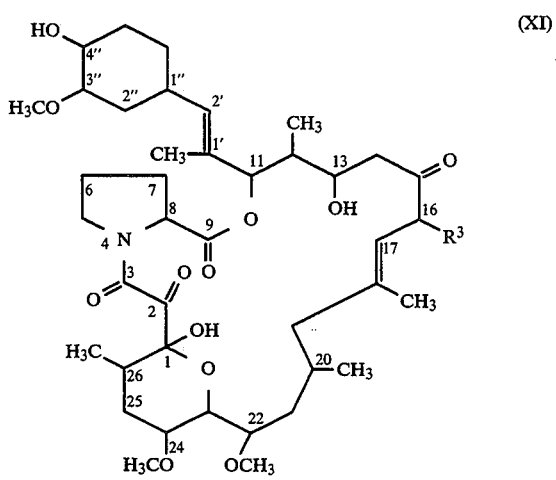

(XI)

by reaction with a diazaphosphonate derivative of the formula

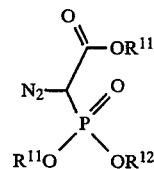

in a reaction inert solvent. The coupling (or phosphonation) reaction of the diazaphosphonate and the macrolide of formula X or XI is facilitated by the addition of a rhodium acetate catalyst.

The expression "reaction inert solvent" when used above and hereinafter refers to any solvent which does not interact with starting materials, reagents, intermediates or products in a manner which adversely affects the yield of the desired product. Suitable such solvents for this reaction include chlorinated solvents such as chloroform, dichloromethane and 1,2-dichloroethane; ether solvents such as diethyl ether, tetrahydrofuran or dioxane, aromatic solvents such as benzene, toluene or xylene; and dipolar aprotic solvents such as N,N-dimethylformamide, acetonitrile and N-methylpyrrolidone. The solvents may be employed singly, or as a combination of solvents. The most preferred solvent is benzene. Generally, it is desirable to employ enough solvent such that the reactants are dissolved in or suspended by the solvent. Typically, the amount of solvent used is varied to give a $10^{-1}$ to $10^{-3}$ Molar solution of macrolide with a $10^{-2}$ Molar solution of macrolide being preferred.

The temperature of the reaction mixture may range from about −20° C. to about 100° C. Generally, the preferred temperature is a temperature of about 10° C. to about 50° C. Dry conditions are maintained throughout the course of the reaction by the utilization of anhydrous solvents, by the maintenance of a reaction inert atmosphere or by the introduction of a drying agent to the reaction mixture. The term "reaction inert atmosphere", where used above and hereafter, is meant to define an atmosphere which does not interact with the starting materials, reagents, intermediates or products in a manner which adversely affects the yield of the desired product. Suitable reaction inert atmospheres include argon atmospheres and nitrogen atmospheres. Argon is generally preferred.

The compounds of the invention have acidic groups which form salts with bases. These salts may be formed by methods well known to those skilled in the art. In general, the base and the free acid are usually combined in a co-solvent from which the desired salt precipitates or can be otherwise isolated by concentration and/or addition of a non-solvent.

The production of macrolides of formulae X and XI is well-known in the literature. The generally preferred route to these macrolides is via biological fermentation of microorganisms belonging to the genus Streptomyces. The compounds of formulae (X) and (XI) wherein $R^3$ is allyl are obtained by fermentation of *Streptomyces tsukubaensis* No. 9993 (Ferm BP-927). The compound of formula X wherein $R^3$ is ethyl and the compound of formula (X) wherein $R^3$ is methyl are obtained by fermentation of *Streptomyces hygroscopicus* subsp. ascomyceticus ATCC 14891.

A lyophilized sample of *Streptomyces hygroscopicus* subsp. ascomyceticus ATCC 14891 has been deposited with the American Type Culture Collection, 12301 Parklawn Drive, Rockville, Md., 20852, U.S.A., under the terms of the Budapest Treaty on Jan. 13, 1992. This newly deposited culture was given the new deposit number of ATCC 55276.

*Streptomyces tsukubaensis* No. 9993 (Ferm BP-927) is currently on deposit with the Fermentation Research Institute, Agency of Industrial Science and Technology (No. 1-3, Higashi-1-chome, Yatabemachi, Tsukuba-gun, Ibaraki Prefecture, Japan), under the provisions of the Budapest Treaty. A fresh sample of the microorganism will be deposited with the American Type Culture Collection in accordance with the terms of the Budapest Treaty.

The above-mentioned microorganisms, when placed separately in aqueous nutrient media, will produce the aforementioned compounds of formula X and XI. The fermentation of said microorganisms to produce these macrolides is accomplished substantially as disclosed in U.S. Pat. No. 4,894,366 issued on Jan. 16, 1990, which is hereby incorporated by reference in its entirety. Any changes made to the disclosed procedure are made in order to accommodate existing equipment at the facility and are described in Preparations 1 and 2 hereinbelow.

The active compounds of this invention prepared by the methods described above, and their pharmaceutically acceptable salts (hereinafter referred to as "the active compounds of this invention") are useful in the treatment of resistance to transplantation or the treatment of autoimmune diseases such as rheumatoid arthritis or psoriasis. In the treatment of resistance to transplantation, the active compounds of this invention may be used either prophylactically or in response to an adverse reaction by the human subject to a transplanted organ or tissue. When used prophylactically, the active compounds of this invention are administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, the active compounds of this invention are administered directly to the patient in order to treat said resistance to transplantation after outward signs of the resistance have been manifested.

For use in the treatment of resistance to transplantation and autoimmune diseases such as rheumatoid arthritis or psoriasis in a mammal, including man, the active compounds of this invention are formulated into a suitable pharmaceutical compositions containing a disease treating effective amount of a compound of formula I. Depending upon the potency of the particular compound being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated, as where the patient is suffering from a skin disease such as psoriasis or whenever the medication is best applied to the surface of a tissue or organ as determined by the attending physician.

The active compounds of this invention are also useful in the treatment of infections caused by fungi. For use in the treatment of said fungal infections in a mammal, including man, the active compounds of this invention are formulated into a pharmaceutical composition containing a disease treating effective amount. Depending upon the potency of the particular compound being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated whenever the medication is best applied to the surface of a tissue or organ as determined by the attending physician.

The active compounds of this invention are generally administered in the form of a pharmaceutical composition comprising at least one of the compounds of formula I, or a pharmaceutically acceptable salt thereof, together with a pharmaceutically acceptable vehicle or diluent. Such compositions are generally formulated in a conventional manner utilizing solid or liquid vehicles or diluents as appropriate to the mode of administration: for oral administration, in the form of tablets, hard or soft gelatin capsules, suspensions, granules, powders and the like; for parenteral administration, in the form of injectable solutions or suspensions and the like; and for topical administration, in the form of solutions, lotions, ointments, salves and the like.

The utility of the compounds of the present invention as medical agents in the treatment of resistance to transplantation, fungal infectious diseases and autoimmune diseases such as rheumatoid arthritis or psoriasis is demonstrated by the activity of said compounds in the biological assays described hereinbelow. Said biological assay also provides a means whereby the activities of the active compounds of this invention can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to elicit a non-specific immune response which is measured via 3H-thymidine uptake. This screen uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 enriched with: 0.5% MEM non-essential amino acids (100×) solution, 1% L-glutamine (200 mM), 1% MEM vitamins (100×), 1% penicillin streptomycin solution (10,000 units/mL) and 15% heat-inactivated human AB serum (NABI). The cells are counted and the concentration is adjusted to $5 \times 10^5$ cells/mL. The solution is then transferred to round bottom 96 well plates in 100 μL/well quantities. These plates now contain the responder cells.

The stimulator cells are prepared by pooling the mononuclear cells collected from several different individuals. The cells are suspended in 90% human AB serum and 10% dimethyl sulfoxide (DMSO) such that the cell count is $2 \times 10^7$ cells/mL. The cells are stored in liquid nitrogen. For an MLR, the viable cells are diluted to $5 \times 10^5$ cells/mL, and 100 μL/well is added to the plates containing the responder cells. To each well, containing a mixture of responder cells and stimulator cells, is added 50 μL of compound solution. Triplicate wells are run for each dose. The plates are incubated at 37° C. under an atmosphere of 5% carbon dioxide ($CO_2$) and are humidified for five days. To each well is added 1 microcurie (μCi) of $^3$H-thymidine and incubation is continued for another eighteen hours. The cells are harvested using the LKB Beta Plate system.

The percent inhibition of stimulated control is obtained using the following equation:

$$\% \text{ Inhibition} = \left[ 100 - \left( \frac{\text{avg. cpm of drug}}{\text{avg. cpm of stimulated control}} \right) \right] \times 100$$

The abbreviation cpm is defined as counts per minute. RPMI-1640 is a tissue culture medium which is available from Sigma.

Activity in the MLR screen recited above is indicative of usefulness of the active compound in the treatment of resistance to transplantation and autoimmune diseases such as rheumatoid arthritis and psoriasis. The compounds of the invention have a 50% inhibition in the MLR screen at a dose of 1 nanamolar (nm).

Antimicrobial activities of the macrolides of the present invention against various fungi are determined by a serial agar dilution method in a Sabouraud agar. Minimum inhibitory concentrations (MIC) are obtained after incubation for 24 hours at 30° C.

The present invention is illustrated by the following examples. However, it should be understood that the invention is not limited to the specific details of these examples. All reactions are conducted under an inert atmosphere, such as argon, unless otherwise specified. The abbreviations THF, DMSO, DAST, DMAP and Ac, where used, refer to tetrahydrofuran, dimethyl sulfoxide, dimethylamino sulfurtrifluoride, 4-dimethylaminopyridine and acetyl, respectively. Anhydrous solvents were used, anhydrous being defined as substantially free from water.

Terms or acronyms which appear in Preparations 1 and 2 are described in further detail hereinbelow.

PYEA agar is prepared by dissolving Difco maltose (10 g), Difco yeast extract (4 g), dextrose (4 g), Difco agar (15 g) and fresh coconut milk (50 mL) in enough deionized water to yield a one liter solution; and the solution is adjusted to pH 7.3 with 1N sodium hydroxide (NaOH).

ATCC 172 medium is prepared by dissolving glucose (10 g), soluble starch (20 g), yeast extract (5 g), NZ-amine A (Difco, 5 g) and calcium carbonate (1 g) in enough deionized water to yield a one liter solution; and the solution is adjusted to pH 7.0 with 1N potassium hydroxide (KOH).

JDYTT medium is prepared by dissolving cerelose (10 g), corn starch (5 g), corn steep liquor (5 g), NZ-amine YTT (5 g), cobalt chloride (0.002 g) and calcium carbonate (3 g) in enough deionized water to yield a one liter solution; and the solution is adjusted to pH 7.2 with 1N NaOH.

NZ-amine A and NA-amine YTT are available from Difco, as are most of the ingredients of the above media.

In the MLR protocol provided hereinabove, RPMI-1640 is a standard medium for MLR studies; MEM is defined as "minimum essential media"; and NABI is a supplier.

The following examples are given for the purpose of illustrating the present invention and should not be construed as being limitations on its scope.

PREPARATION 1

17-Ethyl-1,14-dihydroxy-12-[2'-(4''-hydroxy-3''-methoxy-cyclohexyl)-1'-methylvinyl]-23,25-dimethoxy-13,19,21,27-tetramethyl-11,28-dioxa-4-azatricyclo[22.3.1.0$^4$]-octacos-18-ene-2,3,10,16-tetraone: (FK-520)

*Streptomyces hygroscopicus* subsp. ascomyceticus culture ATCC 14891 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C., and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½ mL of broth. The tubes were frozen at −80° C. during storage.

The tubes from the ultra cold stock were used as seed inoculum for the preparation of inoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N sodium hydroxide (NaOH). The shake flasks were shaken and incubated on a rotary shaker at about 150–200 cycles/minute and 28° C.

Two mL of an about 3 to 5 day-old shake flask inoculum was used to inoculate the second stage flask inoculum containing 80 mL of JDYTT medium in a 3 L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After inoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The product was found primarily in the mycelium, but workup of the whole broth is preferred. Thus, after the fermentation has run its course, the whole broth was extracted twice with one-third to one-half of its volume of methylisobutylketone (MIBK). The layers were separated by means of a DeLaval separator or a Podbielnack extractor. The solvent layer was clarified and concentrated first in a vacuum pan and then in a rotary evaporator. The concentrate was subjected to four tube counter current distribution in 20 liter carbuoys using 10 liter top layer and 1 liter bottom layer per carbuoy of a heptane/acetonitrile 10/1 system. The active bottom layers were collected, combined and concentrated. The material was further purified via filtration through Florisil (washing with hexane, hexane/methylene chloride and methylene chloride, successively, with a gradual increase in methylene chloride). Most of the activity was found in the methylene chloride fractions. These were combined and concentrated. A second filtration step was performed, this time through silica gel (washing with heptane, methylene chloride, methylene chloride/ethyl acetate and ethyl acetate). The activity was mostly found in the fractions containing a methylene chloride/ethyl acetate mixture and the fractions containing only ethyl acetate. These were combined and concentrated, redissolved in methylene chloride and treated with activated charcoal (DARCO G60). The sample was then divided into 12 to 15 g portions and each sample was further chromatographed on a Prep 500 liquid chromatograph using silica gel columns and eluting using a linear gradient beginning with 100% methylene chloride and ending with 100% ethyl acetate. The active cuts were combined, concentrated and chromatographed on a Prep 500, using reversed phase ($^{18}$C) silica gel and eluting with a linear gradient beginning with acetone and ending with 100% water. Clean product was obtained as the last component isolated off the column.

The active fractions in the foregoing fermentation procedure were determined using the following bioassay.

A 12.5 mm disc was applied directly to the agar surface. *Candida albicans* ATCC 14053, *Saccharomyces pastorianus* FD3737 and a sensitive strain of *Byssochlamys fulva* FM 10,300(S) and FM 10,464(R) were used. The Candida and Saccharomyces plates were incubated at 37° C. for 18 hours, then the plates were examined for activity. The Byssochlamys plates were incubated at 28° C. and read after 18 hours. Plates containing only FK506 and FK520 were active against the Byssochlamys strain. Impure fractions (containing nigericin) were active against the other strains as well.

An HPLC method for determining the purity of the fractions was also used. The method entailed using a Dupont Zorbax CN column (4.6 mm×25 cm) and an isocratic system composed of 55/45 water/acetonitrile and a flow rate of one mL/min. Detection was accomplished at 214 nm. The broth sample (20 mL) was mixed with methyl isobutyl ketone (MIBK) (20 mL) and shaken for about 4 to 5 minutes. The layers were separated and the solvent was concentrated to near dryness. The residue was taken up in 1 mL of neat acetonitrile and a 5 μL sample was injected into the HPLC. The retention time for FK520 is approximately 12.7 minutes under these conditions.

PREPARATION 2

17-Allyl-1,14-dihydroxy-12-[2'-(4'''-hydroxy-3''-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone: FK-506

*Streptomyces tsukubaensis* No. 9993 FERM BP-927 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C., and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½ m L of broth. The tubes were frozen at −80° C. during storage.

The tubes from the ultra cold stock were used as seed inoculum for the preparation of inoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N NaOH. The shake flasks were shaken and incubated on a rotary shaker at about 150-200 cycles/minute and 28° C.

Two mL of an about 3 to 5 day-old shake flask inoculum was used to inoculate the second stage flask inoculum containing 80 mL of JDYTT medium in a 3 L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After inoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The fermenters were stopped and extracted twice with ½ its volume of methylisobutylketone (MIBK). The solvent layer was separated by aspiration and concentration in vacuo to a viscous oil. The oil was triturated with hexane, diethyl ether and methylene chloride and the active cuts (the diethyl ether cuts) were chromatographed on florisil. The florisil was eluted with, successively, diethyl ether methylene chloride, ethyl acetate and acetone. The eluate was concentrated and treated with activated charcoal. The concentrate was filtered and dissolved in ethyl acetate. Hexane was added to crystallize the product.

The bioactivity of the broth and subsequent recovery streams was followed by using a strain of *Byssochlamys fulva*. The components in the broth and recovery streams were visualized by chromatography on Analtech silica gel GF (Trademark) plates using neat ethyl acetate as the eluant. The developed plates were sprayed with vanillin reagent (3 g of vanillin in 75 mL of ethanol and 25 mL of 85% phosphoric acid) and heated to 80° C. The product appeared as a violet spot.

EXAMPLE I

17-Ethyl-1,14-dihydroxy-12-[2'-(4''-α,α--ethylacetyl-1-diethylphosphonate-1-methylether-3''-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of FK-520 (198 mg) and diazophosphonate (198 rag) in benzene (5 ml), under a nitrogen atmosphere was added rhodium acetate catalyst (11 mg). The reaction was allowed to proceed at room temperature for 2 hours at which time the solvent was evaporated at reduced pressure.

The residue was flash chromatographed on a silica gel column (2×25 cm) eluted with 60% ethyl acetate/40% hexane.

The title compound was recovered as a blue-green oil (74 rag). (PMR (CDCl$_3$) δ=4.64 (doublet, J=20 Hz); $^{31}$P NMR δ=−94.5, −97.0).

EXAMPLE II

17-Ethyl-1,14-dihydroxy-12-[2'-(4''-bis-α,α-ethylacetyl-1-diethylphosphonate-1-methylether-3''-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The column from Example I was further eluted with 60% ethyl acetate/40% hexane to yield the title compound as a more polar blue green oil (47 mg). (PMR (CDCl$_3$) δ=4.64 (doublet, J=20 Hz), and δ=5.12, 5.16 (2 doublets, J=20 Hz); $^{31}$P NMR δ=−95.5, −97.0, −100.0, −113.5.; FAB MS (+NaI) 1146 (M+Na) and 1036 (M+Cs).

EXAMPLE III

17-Ethyl-1,14-dihydroxy-12-[2'-(4''-α,α--ethylacetyl-1-diethylphosphonate-1-methylether-3''-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of FK-520 (1.58g, 2 mmoles) in 50 ml benzene at room temperature under a nitrogen atmosphere was added diazophosphonate (1.50 g, 6 mmoles), followed by rhodium acetate catalyst (88 rag, 0.2 mmoles). After 5 minutes (min) the catalyst went into solution and the temperature of the solution was raised to reflux. After 4 hours, thin layer chromatography (TLC) indicate 3 new spots. The reaction was cooled to room temperature and the solvent removed under reduced pressure.

The residue was diluted with ethyl acetate (100 ml) and the resulting solution was washed three times with 10% disodium ethylenediaminetetraacetic acid (25 ml), followed by a water wash, and a brine wash. The ethyl acetate solution was then dried over magnesium sulfate (MgSO$_4$). The solvent was removed under reduced pressure to yield a pale green glass-like solid.

The residue was flash chromatographed on a silica gel column (2×25 cm) eluted with 60% ethyl acetate/40% hexane.

The title compound was recovered as an oil (328 mg). (PMR (CDCl$_3$) δ=4.64 (doublet, J=20 Hz); $^{31}$P NMR δ=−94.5, −97.0).

EXAMPLE IV

17-Ethyl-1,14-dihydroxy-12-[2'-(4''-bis-α,α-ethylacetyl-1-diethylphosphonate-1-methylether-3''-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The column from Example III was further eluted with 60% ethyl acetate/40% hexane to yield the title compound as a more polar gray foam (453 mg). (PMR (CDCl$_3$) δ=4.64 (doublet, J=20 Hz), and δ=5.12, 5.16 (2 doublets, J=20 Hz); $^{31}$P NMR δ−95.5, −97.0, −100.0, −113.5.; FAB MS (+NaI) 1146 (M+Na) and 1036 (M+Cs).

EXAMPLE V

17-Ethyl-1,14-dihydroxy-12-[2'-(4''-α,α-ethylacetyl-1-dibenzophosphonate-1-methylether-3''-methoxy-cyclohexyl)-1'-methylvinyl]-23,25-dimethoxy-13,19,21,27-tetramethyl-11,28-dioxa-4-azatricyclo[22.3.1.0<sup>4,9</sup>]-octacos-18-ene-2,3,10,16-tetraone FK-520 (83 mg, 0.105 mmol.) and dibenzodiazophosphonate (85 mg, 0.211 mmol.) were dissolved in benzene (3 ml) under a nitrogen atmosphere. To this solution was added rhodium acetate catalyst (5 mg). The resulting suspension was heated to reflux. After 2.5 hours the reaction was cooled and diluted with ethyl acetate (10 ml), and washed twice with 10% disodium ethylenediaminetetraacetic acid (10 ml) followed by washing with saturated sodium bicarbonate and brine. The ethyl acetate layer was dried over magnesium sulfate (MgSO$_4$) filtered and concentrated under reduced pressure to yield 168 mg of an oil.

The oil was flashed chromatographed on silica gel column (2×20 cm) using 50% ethyl acetate/50% hexane, to yield 28 mg of the title compound. (PMR (CDCl$_3$) δ=4.7 J=17 Hz; $^{31}$P NMR (CDCl$_3$) δ=−95.4).

EXAMPLE VI

17-Ethyl-1,14-dihydroxy-12-[2'-(4''-α,α-ethylacetyl-1-diphosphonicacid-1-methylether-3''-methoxy-cyclohexyl)-1'-methylvinyl]-23,25-dimethoxy-13,19,21,27-tetramethyl-11,28-dioxa-4-azatricyclo[22.3.1.0<sup>4,9</sup>]-octacos-18-ene-2,3,10,16-tetraone The product from Example V above (12 mg) was dissolved in absolute ethanol (5 ml), under nitrogen in a 250 ml Parr bottle. To this solution was added paladium hydroxide catalyst (5 mg). The reaction solution was placed on a Parr shaker under a hydrogen atmosphere (40 psi H$_2$). After 2½ hours, the reaction suspension was filtered through supercel, and the filtrate was concentrated at reduced pressure to yield the title compound (10 mg). (Mass Spectrum M+ +H 989)

We claim:

1. A compound of the formula

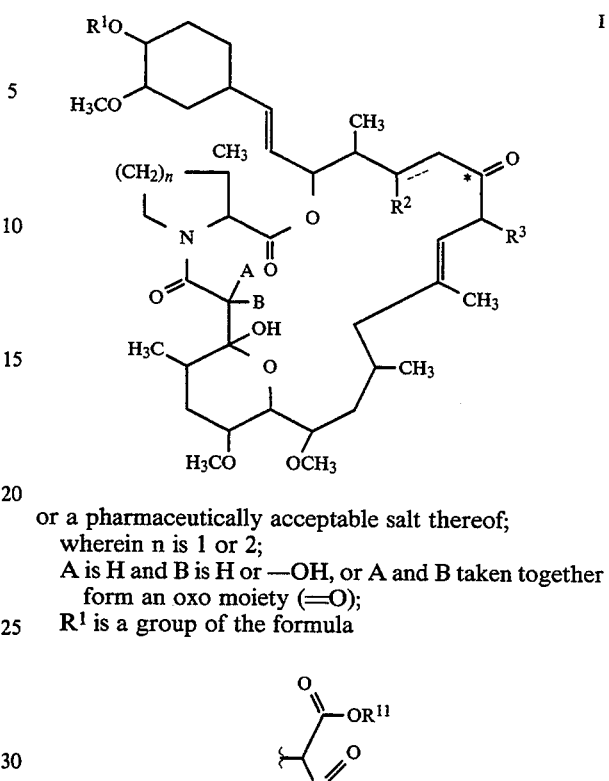

or a pharmaceutically acceptable salt thereof;
wherein n is 1 or 2;
A is H and B is H or —OH, or A and B taken together form an oxo moiety (═O);
R$^1$ is a group of the formula

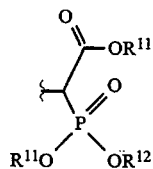

R$^2$ is H or (C$_2$–C$_5$)alkanoyloxy, wherein the dotted line represents an optional double bond in the case where R$^2$ is H;
R$^3$ is (C$_1$ to C$_3$)alkyl or allyl;
R$^{11}$ is independently selected from (C$_1$–C$_3$)alkyl; and
R$^{12}$ is (C$_1$–C$_3$)alkyl or a group of the formula

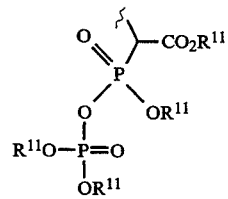

2. A compound of formula I according to claim 1 wherein R$^2$ is —OH and the dotted line represents no bond.

3. A compound of formula I according to claim 1 wherein A and B are taken together and form an oxo moiety (═O), n is 2 and R$^3$ is ethyl.

4. A compound of formula I according to claim 1 wherein R$^1$ is

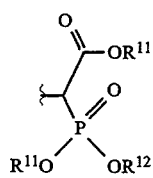

and R$^{12}$ is (C$_1$–C$_3$)alkyl.

* * * * *